(12) United States Patent
Vermeiren et al.

(10) Patent No.: US 8,362,183 B2
(45) Date of Patent: Jan. 29, 2013

(54) MTO PROCESS BASED ON MEAPO MOLECULAR SIEVES COMBINED WITH AN OCP PROCESS TO MAKE OLEFINS

(75) Inventors: Walter Vermeiren, Houthalen (BE); Nikolai Nesterenko, Nivelles (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 269 days.

(21) Appl. No.: 12/530,875

(22) PCT Filed: Mar. 10, 2008

(86) PCT No.: PCT/EP2008/052816
§ 371 (c)(1),
(2), (4) Date: Mar. 4, 2010

(87) PCT Pub. No.: WO2008/110530
PCT Pub. Date: Sep. 18, 2008

(65) Prior Publication Data
US 2010/0184933 A1 Jul. 22, 2010

Related U.S. Application Data

(60) Provisional application No. 60/919,729, filed on Mar. 23, 2007.

(30) Foreign Application Priority Data

Mar. 13, 2007 (EP) .................................. 07104063

(51) Int. Cl.
*C08F 210/00* (2006.01)
*C08F 110/06* (2006.01)
*C08F 110/02* (2006.01)
*C07C 1/00* (2006.01)

(52) U.S. Cl. ........ 526/348; 526/351; 526/352; 585/640; 585/638; 585/639

(58) Field of Classification Search .................. 526/348, 526/351, 352; 585/640, 638, 639
See application file for complete search history.

(56) References Cited

U.S. PATENT DOCUMENTS

4,440,871 A * 4/1984 Lok et al. ...................... 502/214
6,534,692 B1 3/2003 Barger et al.
6,540,970 B1 4/2003 Strohmaier et al.
(Continued)

FOREIGN PATENT DOCUMENTS
WO 9815496 A 4/1998

OTHER PUBLICATIONS

Chen J. et al, "SAPO-18 Catalysts and their Bronsted Acid Sites", Journal of Physical Chemistry, American Chemical Society, U.S., vol. 98, No. 40, 1994, pp. 10216-10221, XP001068798, ISSN: 0022-3654.

*Primary Examiner* — William Cheung (57) ABSTRACT

A process to make light olefins from an oxygen-containing, halogenide-containing or sulphur-containing organic feedstock is disclosed. The process includes contacting the feedstock in a primary reactor with a catalyst that includes a metalloaluminophosphate (MeAPO) molecular sieve to form a first reactor effluent that includes a light olefins and a heavy hydrocarbon fraction. The process further includes separating the light olefins from the heavy hydrocarbon fraction and contacting the heavy hydrocarbon fraction in a second reactor to convert the heavy hydrocarbon fraction to light olefins. The MeAPO molecular sieve is expressed by the formula $H_xMe_yAl_zP_kO_2$ where $y+z+k=1$, x is less than or equal to y, y is from 0.0008 to 0.4, z is from 0.25 to 0.67, and k is from 0.2 to 0.67. The MeAPO molecular sieve has a predominantly plate crystal morphology where the width divided by the thickness is greater than or equal to 10.

34 Claims, 1 Drawing Sheet

U.S. PATENT DOCUMENTS 6,812,372 B2 11/2004 Janssen et al.
6,906,233 B2 * 6/2005 Mees et al. .................... 585/640
2004/0102667 A1 5/2004 Vora et al.
2005/0096214 A1 5/2005 Janssen et al.

* cited by examiner

MTO PROCESS BASED ON MEAPO MOLECULAR SIEVES COMBINED WITH AN OCP PROCESS TO MAKE OLEFINS

The present application is the national stage application of PCT International Application No. PCT/EP2008/052816 filed Mar. 10, 2008, which claims benefit of U.S. Provisional application No. 60/919,729 filed Mar. 23, 2007, which claims foreign priority of EP 07104063.8 filed Mar. 13, 2007.

FIELD OF THE INVENTION

The present invention relates to an MTO (methanol to olefins) process based on MeAPO molecular sieves combined with an OCP (olefins cracking process) process to make olefins. More precisely the MTO process is based on a metalloaluminophosphate (MeAPO) molecular sieve catalyst with lamellar crystal morphology. The limited supply and increasing cost of crude oil has prompted the search for alternative processes for producing hydrocarbon products. One such process is the conversion of methanol to hydrocarbons and especially light olefins. The interest in the methanol to olefin (MTO) process is based on the fact that methanol can be obtained from coal or natural gas by the production of synthesis gas which is then processed to produce methanol. The MTO process produces light olefins such as ethylene and propylene as well as heavy hydrocarbons such as butenes and above. These heavy hydrocarbons are cracked in an OCP process to give mainly ethylene and propylene.

BACKGROUND OF THE INVENTION

The MTO process has been described in US 2006 0235251, WO 2005 016856, US 2006 0063956, US 2006 0161035, U.S. Pat. No. 6,207,872, US 2005 0096214, U.S. Pat. No. 6,953,767 and U.S. Pat. No. 7,067,095.

Ethylene and propylene are particularly desirable olefins but it has been found that their yields in the MTO process are reduced by the production of medium weight hydrocarbons such as $C_4$, $C_5$ and $C_6$ olefins, as well as some heavier components. Methods are needed to alter the product distribution in the MTO process for making light olefins to provide processing flexibility. Methods are sought to reduce the production of $O_4$, $C_5$ and higher olefins from the MTO process relative to the production of ethylene and propylene. Therefore an OCP process is combined with the MTO process to crack the $C_4$, $C_5$ and higher olefins from the MTO process. Such yield improvements of ethylene and propylene significantly improve the economies of the methanol to olefins process.

WO1999 018055 relates to a method for increasing light olefin yield during conversion of oxygenates to olefins comprising: contacting an oxygenate feed in a first reactor (MTO reactor) with a non-zeolitic molecular sieve catalyst under first conditions effective to produce a first product comprising light olefins and a heavy hydrocarbon fraction; separating said light olefins from said heavy hydrocarbon fraction; feeding said heavy hydrocarbon fraction to a second reactor; and subjecting said heavy hydrocarbon fraction in said second reactor to second conditions effective to convert at least a portion of said heavy hydrocarbons to light olefins. Suitable SAPO's for use in the MTO reactor include SAPO-11, SAPO-44, SAPO-34, SAPO-17, and SAPO-18. A preferred zeolite for the auxiliary reactor is ZSM-5.

US 2004 0102667 relates to a process for the production of light olefins from an oxygenate-containing feed stream. This invention more particularly refers to a process for increasing yields of light olefins through cracking of heavier olefins produced in a methanol to olefins process.

It has been discovered that, in a combined MTO OCP process, the use of a specific catalyst in the MTO reactor leads to very high yields in propylene. Said specific catalyst is made of metalloaluminophosphate (MeAPO) molecular sieve with lamellar crystal morphology having an empirical chemical composition on an anhydrous basis, after synthesis and calcination, expressed by the formula $H_xMe_yAl_zP_kO_2$ wherein, $$y+z+k=1$$

$$x \le =y$$

y has a value ranging from 0.0008 to 0.4 and advantageously from 0.005 to 0.18
z has a value ranging from 0.25 to 0.67 and advantageously from 0.38 to 0.55
k has a value ranging from 0.2 to 0.67 and advantageously from 0.36 to 0.54
said molecular sieve having predominantly a plate crystal morphology in which the width (W) and the thickness (T) are such as:
W/T is >=10 and advantageously ranges from 10 to 100.
In a preferred embodiment T is <=0.15 µm, more desirably <=0.10 µm, more desirably <=0.08 µm, advantageously ranges from 0.01 to 0.07 µm and preferably from 0.04 to 0.07 µm.

Said MeAPO are prepared in the presence of one template, one texture influencing agent, inorganic metal source, Al and P source, all these ingredients being in specific proportions, MeAPO with very thin lamellar plate crystal morphology are obtained. The template can be tetraethylammonium hydroxide (TEAOH) or an amine. The texture influencing agent can be an alcohol, a diol or glycerol.

The following prior arts describe MeAPO but they are not in the shape of thin lamellas. All these prior arts concern MeAPO with lamellar cubic or plate crystal morphology. In all these prior arts only one template is used. Moreover the combination MTO-OCP is not described.

U.S. Pat. No. 4,440,871 describes microporous crystalline silicoaluminophosphates (referred as SAPO) the pores of which are uniform and have nominal diameters of greater than about 3 Angstroms and whose essential empirical chemical composition in the as-synthesized and anhydrous form is $mR:(Si_xAl_yP_z)O_2$ wherein "R" represents at least one organic templating agent present in the intracrystalline pore system; "m" has a value of from 0.02 to 0.3; "m" represents the moles of "R" present per mole of $(Si_xAl_yP_z)O_2$; "x", "y" and "z" represent the mole fractions of silicon, aluminum and phosphorus respectively, present as tetrahedral oxides, said mole fractions being such that they are within a specific area in the ternary diagram $Si_xAl_yP_z$. Process for preparing said SAPO comprises forming a reaction mixture containing reactive sources of $SiO_2$, $Al_2O_3$, and $P_2O_5$ and an organic templating agent, said reaction mixture having a composition expressed in terms of molar oxide ratios of: $aR_2O:(Si_xAl_yP_z)O_2:bH_2O$ wherein "R" is an organic templating agent; "a" has a value large enough to constitute an effective amount of "R" and is within the range of greater than 0 to 3; "b" has a value of from zero to 500; "x", "y" and "z" represent the mole fractions, respectively, of silicon, aluminum and phosphorus in the $(Si_xAl_yP_z)O_2$ constituent and each has a value of at least 0.01 and crystallizing the reaction mixture thus formed at a temperature of at least 100° C. until crystals of the silicoaluminophosphate are formed.

U.S. Pat. No. 6,207,872 relates to a process for converting methanol to light olefins comprising contacting the methanol with a catalyst at conversion conditions, the catalyst comprising a crystalline metallo aluminophosphate molecular sieve having a chemical composition on an anhydrous basis expressed by an empirical formula of: $(EL_xAl_yP_z)O_2$ where EL is a metal selected from the group consisting of silicon, magnesium, zinc, iron, cobalt, nickel, manganese, chromium and mixtures thereof, "x" is the mole fraction of EL and has a value of at least 0.005, "y" is the mole fraction of Al and has a value of at least 0.01, "z" is the mole fraction of P and has a value of at least 0.01 and x+y+z=1, the molecular sieve characterized in that it has predominantly a plate crystal morphology, wherein the average smallest crystal dimension is at least 0.1 micron and has an aspect ratio of less than or equal to 5.

U.S. Pat. No. 6,334,994 relates to a microporous crystalline silico-alumino-phosphate composition, the theoretical composition of which, on a water-free basis after synthesis and calcination, is: $H_wSi_xAl_yP_zO_2$ where w and x have a value between 0.01 and 0.05 and y and z are values between 0.4 and 0.6, wherein the composition is a mixed phase product comprising silico-alumino-phosphates of AEI and CHA structure prepared in one batch crystallization, not including mere physical mixtures, the product after calcination in air at 550° C. for 4 hours, produces a specific X-ray diffractogram and XRD-profiles.

EP 893159 relates to a method for preparing catalysts comprising silica-modified crystalline silicoaluminophosphate molecular sieves, which comprises adding an aluminum alkoxide to an aqueous amine or organic ammonium salt solution cooled at a temperature of not higher than 20° C., followed by hydrolysis, until a uniform aqueous aluminum hydroxide colloid or solution is formed, adding, to the colloid or solution, silica or other Si-source compounds, and phosphoric acid or other P-source compounds, if desired, along with a metal source selected from the group of Li, Ti, Zr, V, Cr, Mn, Fe, Co, Zn, Be, Mg, Ca, B, Ga and Ge, hydrothermally treating the resulting mixture to prepare a crystalline silicoaluminophosphate molecular sieve, and then modifying the crystalline silicoaluminophosphate molecular sieve with silica.

US 2005 0096214 (U.S. Pat. No. 6,953,767) relates to a process for making an olefin product from an oxygenate feedstock comprising contacting said oxygenate feedstock with a catalyst comprising a silicoaluminophosphate molecular sieve comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said silicoaluminophosphate molecular sieve, under conditions effective to form an olefin product.

It also describes a method for preparing the molecular sieve of said process that comprises (a) combining a reactive source of silicon, a reactive source of phosphorus and a hydrated aluminum oxide in the presence of an organic structure directing agent (template) to form a mixture;

(b) mixing and heating continuously the mixture prepared at step a) up to the crystallization temperature;

(c) maintaining the mixture at the crystallization temperature and under stirring for a period of time of from 2 to 150 hours;

(d) recovering crystals of the silicoaluminophosphate molecular sieve (e) wherein the mixture prepared at step a) has a molar composition within the following ranges:
$P_2O_5:Al_2O_3$ from 0.6:1 to 1.2:1
$SiO_2:Al_2O_3$ from 0.005:1 to 0.35:1
$H_2O:Al_2O_3$ from 10:1 to 40:1
and the template is a tetraethylammonium compound.

In all these above prior arts only template and/or specific reaction conditions are used to influence the crystal structure of the material. In the following U.S. Pat. No. 6,540,970 a template and a solvent of the metal (Me) source are used. In the examples the organic silicon source is tetraethylorthosilicate. U.S. Pat. No. 6,540,970 relates to a method for making a metalloaluminophosphate (MeAPO) molecular sieve, said process comprising the steps of:

providing a source of alumina, a source of phosphorus, water, and a template suitable for forming a MeAPO molecular sieve;

providing a source of metal including metal particles, said metal particles measuring, in their largest dimension, equal to or less than five nanometers;

providing a water soluble organic solvent capable of solubilizing said source of metal;

forming a synthesis mixture from said source of alumina, said source of phosphorus, said water, said template, said source of metal, and said solvent;

and forming a MeAPO molecular sieve from said synthesis mixture. Desirably, the water soluble organic solvent capable of solubilizing the source of the metal is selected from the group consisting of sulfoxides and $C_1$ to $C_5$ oxygenated hydrocarbons. Desirably, the oxygenated hydrocarbon is selected from the group consisting of alcohols (branched or normal), ketones, aldehydes, diols and acids. Useful solvents include one or more solvents selected from the group consisting of acetone, 1,2-propanediol, 1,3-propanediol, methanol, ethanol, propanol, isopropanol, butanol, and ethylene glycol. Desirably, the solvent is an alcohol. The products obtained are isocrystalline spheroidal particles comprising a SAPO molecular sieve. The particle measures from 0.5 microns to 30 microns in diameter.

BRIEF SUMMARY OF THE INVENTION

The present invention relates to a process to make light olefins from an oxygen-containing, halogenide-containing or sulphur-containing organic feedstock comprising:

contacting said oxygen-containing, halogenide-containing or sulphur-containing organic feedstock in a primary reactor with a catalyst made of a metalloaluminophosphate (MeAPO) molecular sieve with lamellar crystal morphology at conditions effective to convert at least a portion of the feedstock to form a first reactor effluent comprising light olefins and a heavy hydrocarbon fraction;

separating said light olefins from said heavy hydrocarbon fraction;

contacting said heavy hydrocarbon fraction in a second reactor at conditions effective to convert at least a portion of said heavy hydrocarbon fraction to light olefins;

wherein said MeAPO has an empirical chemical composition on an anhydrous basis, after synthesis and calcination, expressed by the formula $H_xMe_yAl_zP_kO_2$ in which, $y+z+k=1$ $x<=y$ y has a value ranging from 0.0008 to 0.4 and advantageously from 0.005 to 0.18 z has a value ranging from 0.25 to 0.67 and advantageously from 0.38 to 0.55 k has a value ranging from 0.2 to 0.67 and advantageously from 0.36 to 0.54 said molecular sieve having predominantly a plate crystal morphology in which the width (W) and the thickness (T) are such as:

W/T is >=10 and advantageously ranges from 10 to 100.

The present invention also relates to a process to make light olefins from an oxygen-containing, halogenide-containing or sulphur-containing organic feedstock comprising:

contacting said oxygen-containing, halogenide-containing or sulphur-containing organic feedstock in a primary reactor with a catalyst made of a metalloaluminophosphate (MeAPO) molecular sieve at conditions effective to convert at least a portion of the feedstock to form a first reactor effluent comprising light olefins and a heavy hydrocarbon fraction;

separating said light olefins from said heavy hydrocarbon fraction;

contacting said heavy hydrocarbon fraction in a second reactor at conditions effective to convert at least a portion of said heavy hydrocarbon fraction to light olefins;

wherein said MeAPO has been prepared by a method comprising:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$, b) crystallizing the above reaction mixture thus formed until crystals of the metalloaluminophosphate are formed, c) recovering a solid reaction product, d) washing it with water to remove the TIA and e) calcinating it to remove the organic template.

DETAILED DESCRIPTION OF THE INVENTION

With regards to the catalyst of the primary reactor, in a preferred embodiment T is <=0.15 μm, more desirably <=0.10 μm, more desirably <=0.08 μm, advantageously ranges from 0.01 to 0.07 μm and preferably from 0.04 to 0.07 μm.

In a advantageous embodiment y has a value ranging from 0.005 to 0.18, z has a value ranging from 0.38 to 0.55 and k has a value ranging from 0.36 to 0.54.

In a first preferred embodiment y has a value ranging from 0.005 to 0.16, z has a value ranging from 0.39 to 0.55 and k has a value ranging from 0.37 to 0.54.

In a second preferred embodiment y has a value ranging from 0.011 to 0.16, z has a value ranging from 0.39 to 0.55 and k has a value ranging from 0.37 to 0.54.

In a third preferred embodiment y has a value ranging from 0.011 to 0.14, z has a value ranging from 0.40 to 0.55 and k has a value ranging from 0.38 to 0.54.

In an advantageous embodiment the MeAPO molecular sieves have essentially a structure CHA or AEI or a mixture thereof. Preferably they have essentially the structure SAPO 18 or SAPO 34 or a mixture thereof.

About the plate crystal morphology, said plates have advantageously the shape of a simple polygon comprised in a square. The square's length is named W. The MeAPO molecular sieves have predominantly a plate crystal morphology. By predominantly is meant advantageously greater than 50% of the crystals. Preferably at least 70% of the crystals have a plate morphology and most preferably at least 90% of the crystals have a plate morphology. About "essentially" referring to the CHA or AEI structure it means that advantageously more than 80% by weight, preferably more than 90%, of the MeAPO of the invention has the structure CHA or AEI or a mixture thereof. About "essentially" referring to the SAPO 18 or SAPO 34 structure it means that advantageously more than 80% by weight, preferably more than 90%, of the MeAPO has the structure SAPO 18 or SAPO 34 or a mixture thereof.

Me is advantageously a metal selected from the group consisting of silicon, germanium, magnesium, zinc, iron, cobalt, nickel, manganese, chromium and mixtures thereof. Preferred metals are silicon, magnesium and cobalt with silicon or germanium being especially preferred.

The MeAPO molecular sieve can be used as itself as a catalyst. In another embodiment it can be formulated into a catalyst by combining the molecular sieve with other materials that provide additional hardness or catalytic activity to the finished catalyst product. Materials which can be blended with the molecular sieve can be various inert or catalytically active materials, or various binder materials. These materials include compositions such as kaolin and other clays, various forms of rare earth metals, alumina or alumina sol, titania, zirconia, quartz, silica or silica sol, and mixtures thereof. These components are effective in densifying the catalyst and increasing the strength of the formulated catalyst. When blended with non-metalloaluminophosphate molecular sieve materials, the amount of MeAPO which is contained in the final catalyst product ranges from 10 to 90 weight percent of the total catalyst, preferably 20 to 70 weight percent of the total catalyst.

With regards to a method to make said MeAPO, it can be made by a method which comprises:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$, said reaction mixture having a composition expressed in terms of molar oxide ratios of:

TEMP/$Al_2O_3$=0.3-5, more desirable 0.5-2
$MeO_2$/$Al_2O_3$=0.005-2.0, more desirable 0.022-0.8
$P_2O_5$/$Al_2O_3$=0.5-2, more desirable 0.8-1.2
TIA/$Al_2O_3$=3-30, more desirable 6-20 b) crystallizing the above reaction mixture thus formed until crystals of the metalloaluminophosphate are formed, c) recovering a solid reaction product, d) washing it with water to remove the TIA and e) calcinating it to remove the organic template.

In an advantageous embodiment TEMP/$Al_2O_3$=0.5-2; $MeO_2$/$Al_2O_3$=0.022-0.8; $P_2O_5$/$Al_2O_3$=0.8-1.2 and TIA/$Al_2O_3$=6-20.

In a first preferred embodiment TEMP/$Al_2O_3$=0.5-2; $MeO_2$/$Al_2O_3$=0.022-0.7; $P_2O_5$/$Al_2O_3$=0.8-1.2 and TIA/$Al_2O_3$=6-20.

In a second preferred embodiment TEMP/$Al_2O_3$=0.7-2; $MeO_2$/$Al_2O_3$=0.05-0.7; $P_2O_5$/$Al_2O_3$=0.8-1.2 and TIA/$Al_2O_3$=6-20.

In a third preferred embodiment TEMP/$Al_2O_3$=0.7-2; $MeO_2$/$Al_2O_3$=0.05-0.6; $P_2O_5$/$Al_2O_3$=0.8-1.2 and TIA/$Al_2O_3$=6-20.

With regards to the TIA, mention may be made, by way of example, of 1,2-propanediol, 1,3-propanediol, methanol, ethanol, propanol, isopropanol, butanol, glycerol or ethylene glycol.

With regards to the organic templating agent, it can be any of those heretofore proposed for use in the synthesis of conventional zeolitic aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms.

Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di and tri-amines are advantageously utilized, either alone or in combination with a quaternary ammonium compound or other templating compound. Representative templating agents include tetramethylammonium, tetraethylammonium, tetrapropylammonium or tetrabutylammonium cations; di-n-propylamine, tripropylamine, triethylamine; diethylamine, triethanolamine; piperidine; morpholine; cyclohexylamine; 2-methylpyridine; N,N-dimethylbenzylamine; N,N-diethylethanolamine; dicyclohexylamine; N,N-dimethylethanolamine; choline; N,N'-dimethylpiperazine; 1,4-diazabicyclo(2,2,2)octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Advantageously organic templating agent is selected among tetraethylammonium hydroxide (TEAOH), diisopropylethylamine (DPEA), tetraethyl ammonium salts, cyclopentylamine, aminomethyl cyclohexane, piperidine, triethylamine, diethylamine, cyclohexylamine, triethyl hydroxyethylamine, morpholine, dipropylamine, pyridine, isopropylamine di-n-propylamine, tetra-n-butylammonium hydroxide, diisopropylamine, di-n-propylamine, n-butylethylamine, di-n-butylamine, and di-n-pentylamine and combinations thereof. Preferably the template, is a tetraethyl ammonium compound selected from the group of tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Most preferably, the template is tetraethyl ammonium hydroxide.

With regards to the reactive inorganic source of $MeO_2$ essentially insoluble in the TIA and relating to silicon, non-limiting examples of useful inorganic silicon source materials non-soluble in alcohols include, fumed silica, aerosol, pyrogenic silica, precipitated silica and silica gel.

With regards to the reactive sources of $Al_2O_3$, it can be any aluminum species capable of being dispersed or dissolved in an aqueous synthesis solution. Useful sources of alumina are one or more sources selected from the group consisting of the following: hydrated alumina, organo alumina, in particularly $Al(OiPr)_3$, pseudo-boehmite, aluminum hydroxide, colloidal alumina, aluminium halides, aluminium carboxylates, aluminium sulfates and mixtures thereof.

With regards to the reactive sources of $P_2O_5$, it can be one or more sources selected from the group consisting of phosphoric acid; organic phosphates, such as triethyl phosphate, tetraethyl-ammonium phosphate; aluminophosphates; and mixtures thereof. The phosphorous source should also be capable of being dispersed or dissolved in an alcohol synthesis solution.

These MeAPO can be prepared by the usual methods of the molecular sieves synthesis technology provided it is in accordance with the above cited ratios. The reaction mixture is in the form of a gel. The ratios $MeO_2/Al_2O_3$ and $P_2O_5/Al_2O_3$ are selected among the above described advantageous and preferred ratios and are in accordance with the advantageous and preferred y, z and k described above. By way of example to make a MeAPO having the y, z and k according to the second preferred embodiment one has to use the ratios of the ingredients according to the second preferred embodiment of the method to make said MeAPO.

With regards to the step b), the reaction mixture obtained by mixing the reactive sources of alumina, $MeO_2$, phosphorus, organic templating agent and TIA is submitted to autogenous pressure and elevated temperature. The reaction mixture is heated up to the crystallization temperature that may range from about 120° C. to 250° C., preferably from 130° C. to 225° C., most preferably from 150° C. to 200° C. Heating up to the crystallization temperature is typically carried for a period of time ranging from about 0.5 to about 16 hours, preferably from about 1 to 12 hours, most preferably from about 2 to 9 hours. The temperature may be increased stepwise or continuously. However, continuous heating is preferred. The reaction mixture may be kept static or agitated by means of tumbling or stirring the reaction vessel during hydrothermal treatment. Preferably, the reaction mixture is tumbled or stirred, most preferably stirred. The temperature is then maintained at the crystallization temperature for a period of time ranging from 2 to 200 hours. Heat and agitation is applied for a period of time effective to form crystalline product. In a specific embodiment, the reaction mixture is kept at the crystallization temperature for a period of from 16 to 96 hours.

With regards to the step c), the usual means can be used. Typically, the crystalline molecular sieve product is formed as a slurry and can be recovered by standard means, such as by sedimentation, centrifugation or filtration.

With regards to the step d), the separated molecular sieve product is washed, recovered by sedimentation, centrifugation or filtration and dried.

With regards to the step e), calcination of molecular sieves is known per se. As a result of the molecular sieve crystallization process, the recovered molecular sieve contains within its pores at least a portion of the template used. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process can be used for partial or complete removal of the template from the intracrystalline pore system.

Additionally, if during the synthesis alkaline or alkaline earth metals have been used, the molecular sieve might be subjected to an ion-exchange step. Conventionally, ion-exchange is done in aqueous solutions using ammonium salts or inorganic acids.

With regards to the MTO process in the primary reactor, typically, the oxygenate feedstock is contacted with the catalyst when the oxygenate is in vapor phase. Alternately, the process may be carried out in a liquid or a mixed vapor/liquid phase. In this oxygenate conversion process, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 575° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygenate compounds and/or mixtures thereof.

The process can be carried out any system using a variety of transport beds, although a fixed bed or moving bed system could be used. Advantageously a fluidized bed is used. It is particularly desirable to operate the reaction process at high space velocities. The process can be conducted in a single reaction zone or a number of reaction zones arranged in series or in parallel. Any standard commercial scale reactor system can be used, for example fixed bed, fluidised bed or moving bed systems. The commercial scale reactor systems can be operated at a weight hourly space velocity (WHSV) of from 0.1 $hr^{-1}$ to 1000 $hr^{-1}$.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

The oxygenate feedstock is any feedstock containing a molecule or any chemical having at least an oxygen atom and capable, in the presence of the above MeAPO catalyst, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. Analogously to these oxygenates, compounds containing sulphur or halides may be used. Examples of suitable compounds include methyl mercaptan; dimethyl sulfide; ethyl mercaptan; di-ethyl sulfide; ethyl monochloride; methyl monochloride, methyl dichloriden-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof. The most preferred oxygenate compound is methanol.

With regards to the primary reactor effluent, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. It is desirable to have a 100% conversion of the oxygenate in the primary reactor. This conversion rate is adjusted by optimization of the regeneration of the catalyst. Typically in the effluent, and not taking account of the diluent or the unconverted oxygenate, composition by weight % (the total being 100%) on carbon basis is as follows:
olefins range from 80 to 98,
paraffins (comprising methane) range from 2 to 20,
dienes range from 0.1 to 0.5,
aromatics are less than 0.5.

Among the olefins, on a 100% basis, the light olefins are from 60 to 95% for respectively 5 to 40% of olefins with 4 carbon atoms or more. Among the light olefins the weight ratio propylene/ethylene is higher than 1.1 and advantageously around 1.1-1.3.

Among the olefins having 4 carbon atoms or more there are 65 to 85 weight % of butenes. More than 85% by weight and advantageously more than 95% of the hydrocarbons having 4 carbon atoms or more are C4 to C8 olefins.

With regards to the OCP process in the second reactor, said process is known per se. It has been described in EP 1036133, EP 1035915, EP 1036134, EP 1036135, EP 1036136, EP 1036138, EP 1036137, EP 1036139, EP 1194502, EP 1190015, EP 1194500 and EP 1363983 the content of which are incorporated in the present invention.

The heavy hydrocarbon fraction produced in the primary reactor (MTO) is converted in the second reactor, also called an "olefin cracking reactor" or OCP herein, to produce additional amounts of ethylene and propylene. Advantageously the catalysts found to produce this conversion comprise a crystalline silicate of the MFI family which may be a zeolite, a silicalite or any other silicate in that family or the MEL family which may be a zeolite or any other silicate in that family. Examples of MFI silicates are ZSM-5 and silicalite. An example of an MEL zeolite is ZSM-11 which is known in the art. Other examples are Boralite D and silicalite-2 as described by the International Zeolite Association (*Atlas of Zeolite Structure Types,* 1987, Butterworths). The preferred crystalline silicates have pores or channels defined by ten oxygen rings and a high silicon/aluminum atomic ratio.

Crystalline silicates are microporous crystalline inorganic polymers based on a framework of $XO_4$ tetrahydra linked to each other by sharing of oxygen ions, where X may be trivalent (e.g. Al, B, ...) or tetravalent (e.g. Ge, Si, ...). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nm and a sinusoidal channel along [100]: 0.51-0.55 nm. Crystalline silicates with the MEL structure possess a bi-directional intersecting straight pore system with straight channels along [100] having pore diameters of 0.53-0.54 nm.

The crystalline silicate catalyst has structural and chemical properties and is employed under particular reaction conditions whereby the catalytic cracking of the $C_4^+$ olefins readily proceeds. Different reaction pathways can occur on the catalyst. Under the process conditions, having an inlet temperature of around 400° to 600° C., preferably from 520° to 600° C., yet more preferably 540° to 580° C., and an olefin partial pressure of from 0.1 to 2 bars, most preferably around atmospheric pressure. Olefinic catalytic cracking may be understood to comprise a process yielding shorter molecules via bond breakage. With such high silicon/aluminum ratio in the crystalline silicate catalyst, a stable olefin conversion can be achieved with a high propylene yield on an olefin basis.

The MFI catalyst having a high silicon/aluminum atomic ratio for use in the second reactor of the present invention may be manufactured by removing aluminum from a commercially available crystalline silicate. A typical commercially available silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefinic cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 300 and most preferably around 480.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free, although aluminum in certain chemical compounds as in $AlPO_4$'s may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica or $AlPO_4$.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, spheres, extruded into other shapes, or formed into a spray-dried powder. In the catalytic cracking process of the second reactor, the process conditions are selected in order to provide high selectivity towards propylene or ethylene, as desired, a stable olefin conversion over time, and a stable olefinic product distribution in the effluent. Such objectives are favored by the use of a low acid density in the catalyst (i.e. a high Si/Al atomic ratio) in conjunction with a low pressure, a high inlet temperature and a short contact time, all of which process parameters are interrelated and provide an overall cumulative effect. The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 5 to 30 $hr^{-1}$, preferably from 10 to 30 $hr^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The heavy hydrocarbon fraction feedstock is preferably fed at a total inlet pressure sufficient to convey the feedstocks through the reactor. Said feedstock may be fed undiluted or diluted in an inert gas, e.g. nitrogen or steam. Preferably, the total absolute pressure in the second reactor ranges from 0.5 to 10 bars. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 400° to 650° C., more preferably from 450° to 600° C., yet more preferably from 540° C. to 590° C., typically around 560° to 585° C.

In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

The second reactor can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors. The heavy hydrocarbon fraction cracking process is endothermic; therefore, the reactor should be adapted to supply heat as necessary to maintain a suitable reaction temperature. Online or periodic regeneration of the catalyst may be provided by any suitable means known in the art.

The various preferred catalysts of the second reactor have been found to exhibit high stability, in particular being capable of giving a stable propylene yield over several days, e.g. up to ten days. This enables the olefin cracking process to be performed continuously in two parallel "swing" reactors wherein when one reactor is operating, the other reactor is undergoing catalyst regeneration. The catalyst can be regenerated several times.

The second reactor effluent comprises methane, light olefins and hydrocarbons having 4 carbon atoms or more. Advantageously said second reactor effluent is sent to a fractionator and the light olefins are recovered. Advantageously the hydrocarbons having 4 carbon atoms or more are recycled at the inlet of the second reactor, optionally mixed with the heavy hydrocarbon recovered from the effluent of the first reactor. Advantageously, before recycling said hydrocarbons having 4 carbon atoms or more at the inlet of the second reactor, said hydrocarbons having 4 carbon atoms or more are sent to a second fractionator to purge the heavies. In a preferred embodiment the light olefins recovered from the effluent of the first reactor and the light olefins recovered from the fractionator following the second reactor are treated in a common recovery section.

Optionally, in order to adjust the propylene to ethylene ratio of the whole complex, ethylene in whole or in part can be recycled over the second reactor and advantageously converted into more propylene. This ethylene can either come from the fractionation section of the first reactor or from the second reactor.

Optionally, the ethylene in whole or in part coming from either the first or the second reactor can be recycled over the first reactor where it combines with methanol to form more propylene. These ways of operation allow to respond with the same equipment and catalyst to market propylene to ethylene demand.

With regards to another embodiment of the invention, said embodiment relates to a process to make light olefins from an oxygen-containing, halogenide-containing or sulphur-containing organic feedstock comprising:

contacting said oxygen-containing, halogenide-containing or sulphur-containing organic feedstock in a primary reactor with a catalyst made of a metalloaluminophosphate (MeAPO) molecular sieve at conditions effective to convert at least a portion of the feedstock to form a first reactor effluent comprising light olefins and a heavy hydrocarbon fraction;

separating said light olefins from said heavy hydrocarbon fraction;

contacting said heavy hydrocarbon fraction in a second reactor at conditions effective to convert at least a portion of said heavy hydrocarbon fraction to light olefins;

wherein said MeAPO has been prepared by a method comprising:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$, b) crystallizing the above reaction mixture thus formed until crystals of the metalloaluminophosphate are formed, c) recovering a solid reaction product, d) washing it with water to remove the TIA and e) calcinating it to remove the organic template.

In a usual embodiment said reaction mixture has a composition expressed in terms of molar oxide ratios of:

$TEMP/Al_2O_3$=0.3-5, more desirable 0.5-2

$MeO_2/Al_2O_3$=0.005-2.0, more desirable 0.022-0.8

$P_2O_5/Al_2O_3$=0.5-2, more desirable 0.8-1.2

$TIA/Al_2O_3$=3-30, more desirable 6-20

In an advantageous embodiment $TEMP/Al_2O_3$=0.5-2; $MeO_2/Al_2O_3$=0.022-0.8; $P_2O_5/Al_2O_3$=0.8-1.2 and $TIA/Al_2O_3$=6-20.

In a first preferred embodiment $TEMP/Al_2O_3$=0.5-2; $MeO_2/Al_2O_3$=0.022-0.7; $P_2O_5/Al_2O_3$=0.8-1.2 and $TIA/Al_2O_3$=6-20.

In a second preferred embodiment $TEMP/Al_2O_3$=0.7-2; $MeO_2/Al_2O_3$=0.05-0.7; $P_2O_5/Al_2O_3$=0.8-1.2 and $TIA/Al_2O_3$=6-20.

In a third preferred embodiment $TEMP/Al_2O_3$=0.7-2; $MeO_2/Al_2O_3$=0.05-0.6; $P_2O_5/Al_2O_3$=0.8-1.2 and $TIA/Al_2O_3$=6-20.

The metalloaluminophosphate (MeAPO) molecular sieves made with the above method have a lamellar crystal morphology.

In a usual embodiment the metalloaluminophosphate (MeAPO) molecular sieves made with the above method have a lamellar crystal morphology having an empirical chemical composition on an anhydrous basis, after synthesis and calcination, expressed by the formula $H_xMe_yAl_zP_kO_2$ wherein, $$y+z+k=1$$

$$x<=y$$

y has a value ranging from 0.0008 to 0.4 and more desirable from 0.005 to 0.18 z has a value ranging from 0.25 to 0.67 and more desirable from 0.38 to 0.55 k has a value ranging from 0.2 to 0.67 and more desirable from 0.36 to 0.54 said molecular sieve having predominantly a plate crystal morphology.

The values of y, z and k in the usual embodiment are obtained by the ratios of the ingredients described in the usual embodiment method above described.

In an advantageous embodiment y has a value ranging from 0.005 to 0.18, z has a value ranging from 0.38 to 0.55 and k has a value ranging from 0.36 to 0.54.

In a first preferred embodiment y has a value ranging from 0.005 to 0.16, z has a value ranging from 0.39 to 0.55 and k has a value ranging from 0.37 to 0.54.

In a second preferred embodiment y has a value ranging from 0.011 to 0.16, z has a value ranging from 0.39 to 0.55 and k has a value ranging from 0.37 to 0.54.

In a third preferred embodiment y has a value ranging from 0.011 to 0.14, z has a value ranging from 0.40 to 0.55 and k has a value ranging from 0.38 to 0.54.

The values of y, z and k in the advantageous, first, second and third embodiments described above are obtained by using the ingredients ratios described respectively in the advantageous, first, second and third embodiments of the method described above.

In an advantageous embodiment the MeAPO made by the above method have essentially a structure CHA or AEI or a mixture thereof. Preferably they have essentially the structure SAPO 18 or SAPO 34 or a mixture thereof.

All the conditions already cited above relating to the synthesis of the MeAPO, the details of the primary reactor, operating conditions of said primary reactor, the details of the second reactor, operating conditions of said second reactor etc . . . apply to said other embodiment of the invention.

BRIEF DESCRIPTION OF THE FIGURE

FIG. 1 illustrates a specific embodiment of the invention. The effluent of the primary reactor is passed to a fractionator 11. The overhead, a C1-C3 fraction including the light olefins is sent via line 2 to a common recovery section (not shown). The bottoms (the heavy hydrocarbon fraction) are sent via line 3 to the second reactor (OCP reactor). The effluent of the second reactor (OCP reactor) is sent via line 10 to a fractionator 8. The overhead, a C1-C3 fraction including the light olefins, is sent via line 9 to a common recovery section (not shown). The bottoms, hydrocarbons having 4 carbon atoms or more, are sent to a fractionator 5. The overhead, hydrocarbons having 4 to substantially 5 carbon atoms are recycled via line 4 at the inlet of the second reactor. The bottoms, hydrocarbons having substantially 6 carbon atoms or more, are purged via line 6.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized to form polyolefins, particularly polyethylenes and polypropylenes.

EXAMPLES

In the following examples:

EG means ethylene glycol,

Eth means ethanol,

MeOH means methanol,

XRD means X ray diffraction,

SEM means scanning electron microscopy,

Aerosil 200® is a fumed silica supplied by Degussa.

Examples 1-3

A reaction mixture of TIA, phosphoric acid (85% in water) and TEAOH solution (40% in water) was prepared in a teflon vessel. In this solution were added corresponding amount of Al source and Si-source respectively. This slurry was mixed until homogeneous for about 30 min at room temperature. Then the teflon vessel was put into stainless autoclave. This autoclave was kept under temperature. After cooling to room temperature, a sample was taken, washed and dried. Separation of the solid from the liquid phase after synthesis was performed by centrifugation. Separated solid was dried at 110° C. overnight and calcined in air flow at 600° C. for 10 h.

Proportions and operating conditions are in the following table. This procedure was applied for the all examples.

Examples 1-3

Figure 1:
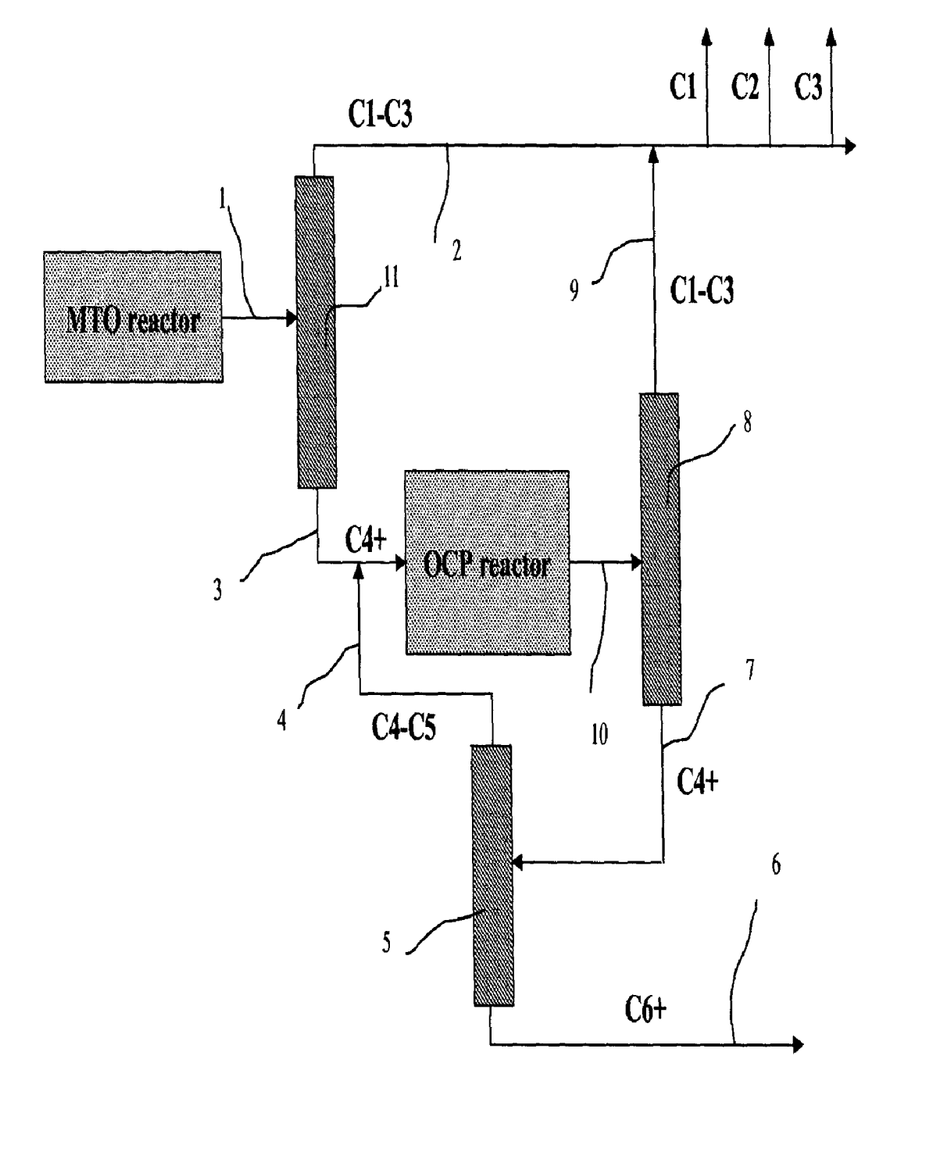

|  | Example | |
|---|---|---|
|  | 1 | 2 |
| molar composition | 1 TEAOH/0.1 $SiO_2$/1 $P_2O_5$/ 1 $Al_2O_3$/12 TIA | |
| TEAOH (35% in water), g | 7.01 | 7.04 |
| Al isopropoxide 98%, g | 6.95 | 6.94 |
| TIA, g | 12.41 EG | 9.22 Eth |
| Aerosil 200, g | 0.10 | 0.11 |
| $H_3PO_4$ (85% in water), g | 3.84 | 3.96 |
| Conditions | 160° C., 3 days | |
| XRD | SAPO-18 | SAPO-18 |
| SEM | Lamellar FIG. 1 | Lamellar |

|  | Example 3 |
|---|---|
| molar composition | 1 TEAOH/0.1 $SiO_2$/0.9 $P_2O_5$/0.9 $Al_2O_3$/12 TIA |
| TEAOH (40% in water), g | 28.03 |
| Al isopropoxide 98%, g | 27.82 |
| TIA, g | 27.81 MeOH |
| Aerosil 200, g | 0.50 |
| $H_3PO_4$ (85% in water), g | 15.80 |
| Conditions | 160° C., 3 days |
| XRD | SAPO-18 |
| SEM | Lamellar |

Examples 4-6

|  | Example 4 |
|---|---|
| molar composition | 1 TEAOH/0.3 $SiO_2$/1 $P_2O_5$/1 $Al_2O_3$/12 TIA |
| TEAOH (35% in water), g | 28.00 |
| Al isopropoxide 98%, g | 27.80 |
| TIA, g | 50.15 EG |
| Aerosil 200 g | 1.34 |
| $H_3PO_4$ (85% in water), g | 15.30 |
| Conditions | 3 days, 160° C. |
| XRD | SAPO-18 |
| SEM | Lamellar |

|  | Example | |
|---|---|---|
|  | 5 | 6 |
| molar composition | 1 TEAOH/0.3 $SiO_2$/0.9 $P_2O_5$/ 0.9 $Al_2O_3$/12 TIA | |
| TEAOH (40% in water), g | 28.03 | 28.03 |
| Al isopropoxide 98%, g | 27.82 | 27.82 |
| TIA, g | 39.99 Eth | 27.81 MeOH |
| Aerosil 200 g | 1.50 | 1.50 |
| $H_3PO_4$ (85% in water), g | 15.80 | 15.80 |
| Conditions | 3 days, 160° C. | |
| XRD | SAPO-18 | SAPO-34 |
| SEM | Lamellar | Lamellar |

Examples 7-8

|  | Example 7 |
|---|---|
| molar composition | 1 TEAOH/0.6 SiO$_2$/1 P$_2$O$_5$/1 Al$_2$O$_3$/12 TIA |
| TEAOH (35% in water), g | 28.10 |
| Al isopropoxide 98%, g | 27.80 |
| TIA g | 50.08 EG |
| Aerosil 200, g | 2.50 |
| H$_3$PO$_4$ (85% in water), g | 15.30 |
| Conditions | 3 days, 160° C. |
| XRD | SAPO-18 |
| SEM | Lamellar |

|  | Example 8 |
|---|---|
| molar composition | 1 TEAOH/0.6 SiO$_2$/0.9 P$_2$O$_5$/0.9 Al$_2$O$_3$/12 TIA |
| TEAOH (40% in water), g | 28.03 |
| Al isopropoxide 98%, g | 27.82 |
| TIA g | 39.99 Eth |
| Aerosil 200, g | 3.06 |
| H$_3$PO$_4$ (85% in water), g | 15.80 |
| Conditions | 3 days, 160° C. |
| XRD | SAPO-34 |
| SEM | Lamellar FIG. 2 |

Example 9

Synthesis at Higher Temperature

|  | Example 9 |
|---|---|
| molar composition | 1 TEAOH/0.3 SiO$_2$/1 P$_2$O$_5$/1 Al$_2$O$_3$/12 TIA |
| TEAOH (35% in water), g | 28.10 |
| Al isopropoxide 98%, g | 27.80 |
| TIA g | 50.08 EG |
| Aerosil 200 g | 1.34 |
| H$_3$PO$_4$ (85% in water), g | 15.50 |
| Conditions | 3 days, 190° C. |
| XRD | SAPO-18 |
| SEM | Lamellar |

Examples 10-11

Reduced Amount of TIA

|  | Example 10 | Example 11 |
|---|---|---|
| molar composition | 1 TEAOH/0.1 SiO$_2$/1 P$_2$O$_5$/1 Al$_2$O$_3$/6 TIA | |
| TEAOH (35% in water), g | 14.02 | 11.06 |
| Al isopropoxide 98%, g | 13.89 | 10.91 |
| TIA g | 12.54 EG | 7.25 Eth |
| Aerosil 200, g | 0.20 | 0.16 |
| H$_3$PO$_4$ (85% in water), g | 7.69 | 6.12 |
| XRD | SAPO-18 | SAPO-18 |
| SEM | Lamellar | Lamellar |

Example 12

Synthesis with Reduced Amount of Template

|  | Example 12 |
|---|---|
| molar composition of gel | 0.7/TEAOH/0.1SiO$_2$/1Al$_2$O$_3$/15EG/1P$_2$O$_5$ |
| TEAOH (35% in water), g | 9.81 |
| Al isopropoxide 98%, g | 13.89 |
| TIA, g | 31.35 EG |
| Aerosil 200, g | 0.20 |
| H$_3$PO$_4$ (85% in water), g | 7.69 |
| Conditions | 160° C., 4 days |
| XRD | SAPO-18 |
| SEM | Lamellar |

Example 13

Synthesis with Increased Amount of Template in Presence of EG

|  | Example 13 |
|---|---|
| molar composition | 2TEAOH/0.1SiO$_2$/1Al$_2$O$_3$/1P$_2$O$_5$/6EG |
| TEAOH (35% in water), g | 28.00 |
| Al isopropoxide 98%, g | 13.90 |
| TIA, g | 12.54 EG |
| Aerosil 200, g | 0.20 |
| H$_3$PO$_4$ (85% in water), g | 7.69 |
| Conditions | 160° C., 4 days |
| XRD | SAPO-18 |
| SEM | Lamellar FIG. 3 |

Example 14

Synthesis at Lower Si-Content

|  | Example 14 |
|---|---|
| molar composition | 1TEAOH/0.05 SiO$_2$/1Al$_2$O$_3$/1P$_2$O$_5$/12EG |
| TEAOH (35% in water), g | 14.00 |
| Al isopropoxide 98%, g | 13.90 |
| TIA, g | 25.08 EG |
| Aerosil 200, g | 0.10 |
| H$_3$PO$_4$ (85% in water), g | 7.7 |
| Conditions | 160° C., 4 days |

|  | Example 14 |
| --- | --- |
| XRD | SAPO-18 |
| SEM | Lamellar |

Comparative Example I

The essential of this recipe: the source of Si must be soluble in alcohol. In the present invention all Si sources are not soluble in TIA.
Synthesis of SAPOs in presence of alcohol with organic source of Si according to U.S. Pat. No. 6,540,970 protocol:

|  | Example comparative example I |
| --- | --- |
| Recipe | U.S. Pat. No. 6,540,970 B1 |
| molar composition | 2TEAOH/0.1SiO$_2$/1Al$_2$O$_3$/1P$_2$O$_5$/50 H$_2$O/8 Eth |
| H$_2$O, g | 19.90 |
| TEAOH (35% in water), g | 60.00 |
| Al source (catapal B), g a hydrated alumina | 10.04 |
| Ethanol, g | 26.28 |
| Si source TEOS, g | 1.52 |
| H$_3$PO$_4$ (85% in water), g | 16.44 |
| Conditions | 195° C., 1 day |
| XRD | SAPO-34/18 |
| SEM | Cubic crystal FIG. 4 |

Morphology of the samples synthesized according to this recipe is different from lamellar. Indeed, a very particular spheroidal morphology has been described in this patent for SAPO-34 sample. The crystallites have a width, at their largest dimension, of from about 0.5 μm to about 30 μm.

Reproduction of example for SAPO-18 synthesis led to materials with cubic crystals.

Comparative Example II

Synthesis of SAPO-18 (Chen's Recipe)

Verified Syntheses of Zeolitic Materials, H. Robson, Elsevier, p. 81,
Catalysis Letters 28 (1994) 241-248
J. Chem. Soc., Chem. Comm., 1994, 603-604
J. Phys. Chem. 1994, 98, 10216-10224

|  | Example Comparative ex II |
| --- | --- |
| Molar composition | 0.4SiO$_2$:1Al$_2$O$_3$:0.9P$_2$O$_5$:50H$_2$O:1.9 DPEA |
| H$_2$0, g | 66.92 |
| H$_3$PO$_4$ (85% in water), g | 16.73 |
| Al source (catapal B), g a hydrated alumina | 11.35 |
| Aerosil 200, g | 1.96 |
| DPEA, g | 20.00 |
| Conditions: | 160° C., 7 days |
| XRD | SAPO-18 |

|  | Example Comparative ex II |
| --- | --- |
| SEM | cubes FIG. 5 |

Comparative Example III

Synthesis of SAPOs According to U.S. Pat. No. 6,334,994 Recipe at High and Low Si Content

|  | Example | |
| --- | --- | --- |
|  | Comparative ex IIIa | Comparative ex IIIb |
| Recipe reference | U.S. Pat. No. 6,334,994 | Microporous Mesoporous 1999, 29, 159 |
| molar composition | 0.075 SiO$_2$/Al$_2$O$_3$/ 0.98 P$_2$O$_5$/ 2 TEAOH | 0.3 SiO$_2$/Al$_2$O$_3$/ 0.98 P$_2$O$_5$/ 2 TEAOH |
| H$_2$0, g | 18.06 | 36.08 |
| Al isopropoxide 98%, g | 13.80 | 27.23 |
| H$_3$PO$_4$ (85% in water), g | 7.52 | 15.17 |
| HCl, g | 0.12 | 0.20 |
| Ludox AS 40 (40% silica), g | 0.54 | 4.00 |
| TEAOH (35% in water), g | 28.20 | 56.08 |
| XRD | SAPO-18 | SAPO-34 |
| SEM | laminated cubes FIG. 6 | cubes FIG. 7 |

Comparative Example IV

U.S. Pat. No. 6,953,767 B2

Inventors in the U.S. Pat. No. 6,953,767B2 described a synthesis of SAPOs phase mixed structure. 18/34 phase ratio was tuned by changing the turning rate of autoclave during the synthesis.

The results showed, that phase composition is reproducible but the morphology was not lamellar.

|  | Example Comparative ex IV same as ex 1 of U.S. Pat. No. 6,953,767 B2 |
| --- | --- |
| molar composition | 0.15 SiO$_2$/1Al$_2$O$_3$/1 P$_2$O$_5$/1TEAOH/35 H$_2$O |
| Conditions | 175° C., 8 h |
| rotation rate, rpm | 60 |
| H$_2$0, g | 32.13 |
| Alumina (Condea Pural SB), g | 19.85 |
| H$_3$PO$_4$, (85% in water), g | 33.55 |
| Ludox AS 40 (40% silica), g | 3.32 |
| TEAOH (35% in water), g | 61.40 |
| TOTAL weight, g | 150.25 |
| XRD | AEI/CHA~0.2 |
| SEM | laminated cubes FIG. 8 |

Example 15

Catalyst tests were performed on 2 g catalyst samples with a pure methanol feed at 450° C., pressure of 0.5 barg, and WHSV=1.6 h$^{-1}$, in a fixed-bed, down flow stainless-steel reactor. Catalyst powders was pressed into wafers and crushed to 35-45 mesh particles. Prior to catalytic run all catalysts were heated in flowing N$_2$ (5 Nl/h) up to the reaction temperature. Analysis of the products has been performed on-line by a gas chromatograph equipped with a capillary column. Catalytic performances of MeAPOs molecular sieves were compared at 100% of methanol conversion and maximum of catalyst activity just before appearance of DME in the effluent.

The feedstock which contains substantially non cyclic olefins C4+ (the heavy hydrocarbon fraction) was subjected to catalytic cracking (the second reactor) in the presence of an aluminosilicate catalyst in a fixed bed reactor at 575° C., LHSV=10 h$^{-1}$, P=1.5 bara. This catalyst comprises a commercially available silicalite which had been subjected to a dealumination treatment by combination of steaming with acid treatment so as provide Si/Al ratio ~250. A detailed procedure of catalyst preparation is described in above cited EP1194502 B1.

The OCP performance has been simulated using a mathematic model employing conversion factors deduced from numerous testing of different feedstocks. Based on the stream composition going to the OCP reactor and on the required purges an optimum stream of C4 and heaviers are recycled around the OCP reactor. The lines under "OCP feed non cyclic olefins C4+" display the heavy hydrocarbon flow rate sent to the OCP (the second reactor). The lines under "MTO+OCP" display the ethylene and propylene produced by the combination of the primary reactor (MTO) and the second reactor (OCP).

The results are in table 1 hereunder. The values in table 1 are the weight percent on carbon basis.

Example 16

Catalyst tests were performed on 2 g catalyst samples with a methanol/H$_2$O: 70/30 feed at 450° C., pressure of 0.2 barg, WHSV=2.9 h$^{-1}$, in a fixed-bed, down flow stainless-steel reactor. Catalyst powders was pressed into wafers and crushed to 35-45 mesh particles. Prior to catalytic run all catalysts were heated in flowing N$_2$ (5 Nl/h) up to the reaction temperature. Analysis of the products has been performed on-line by a gas chromatograph equipped with a capillary column. Catalytic performances of SAPOs molecular sieves were compared at 100% of methanol conversion and maximum of catalyst activity just before appearance of DME in the effluent.

The feedstock which contains C4 and C5 olefins (the heavy hydrocarbon fraction) was subjected to catalytic cracking (the second reactor) in the presence of an aluminosilicate catalyst in a fixed bed pilot plant at 575° C., LHSV=10 h$^{-1}$, P=1.5 bara. This catalyst comprises a commercially available silicalite which had been subjected to a dealumination treatment by combination of steaming with acid treatment so as provide Si/Al ratio ~250. A detailed procedure of catalyst preparation is described in above cited EP1194502 B1. The OCP performance has been simulated using a mathematic model employing conversion factors deduced from numerous testing of different feedstocks. Based on the stream composition going to the OCP reactor and on the required purges an optimum stream of C4 and heaviers are recycled around the OCP reactor. The lines under "OCP feed non cyclic olefins C4+" display the heavy hydrocarbon flow rate sent to the OCP (the second reactor). The lines under "MTO+OCP" display the ethylene and propylene produced by the combination of the primary reactor (MTO) and the second reactor (OCP).

The results are in table 1 hereunder. The values in table 2 are the weight percent on carbon basis.

TABLE 1

|  | SAPO-18 | SAPO-18 | SAPO-18 | SAPO-18 | SAPO-34/18 | SAPO-18 |
|---|---|---|---|---|---|---|
|  |  |  | Morphology |  |  |  |
|  | lamellas EX 1 | lamellas EX 5 | lamellas EX 10 | lamellas EX 14 | cubic comp ex I | cubic comp ex II |
| Methane in the MTO effluent | 2.8 | 1.7 | 2.9 | 2.8 | 4.7 | 4.9 |
| Paraffins including the C1 above | 8.7 | 3.6 | 5.4 | 8.2 | 10.1 | 9.3 |
| Olefins | 90.7 | 95.9 | 94.2 | 91.0 | 85.4 | 85.9 |
| Dienes | 0.4 | 0.2 | 0.4 | 0.2 | 3.8 | 4.2 |
| Aromatics | 0.1 | 0.3 | 0.1 | 0.5 | 0.7 | 0.6 |
| Purity C2's | 99 | 99 | 99 | 98 | 95 | 97 |
| Purity C3's | 99 | 99 | 99 | 99 | 97 | 97 |
| C3/C2 | 1.2 | 1.2 | 1.2 | 1.3 | 1.0 | 1.0 |
| C2 + C3 | 70.4 | 72.7 | 74.3 | 73.2 | 73.2 | 70.8 |
| ethylene in MTO effluent | 32.1 | 33.5 | 34.1 | 31.7 | 36.0 | 35.1 |
| propylene in MTO effluent | 38.3 | 39.2 | 40.2 | 41.5 | 37.3 | 35.7 |
| OCP feed non cyclic olefins C4+ |  |  |  |  |  |  |
| C4 olefins | 14.2 | 15.1 | 14.1 | 9.6 | 7.4 | 8.3 |
| C5 olefins | 4.0 | 4.7 | 3.7 | 3.1 | 2.5 | 4.1 |
| C6 olefins | 1.6 | 2.4 | 1.6 | 0.9 | 1.7 | 2.0 |
| C7 olefins | 0.3 | 0.6 | 0.3 | 0.2 | 0.4 | 0.4 |
| C8 olefins | 0.0 | 0.0 | 0.0 | 0.0 | 0.0 | 0.0 |
| Σ olefins sent to OCP | 20.1 | 22.8 | 19.7 | 13.8 | 12.0 | 14.8 |
| MTO + OCP |  |  |  |  |  |  |
| ethylene | 35.1 | 36.9 | 37.0 | 33.8 | 37.8 | 37.3 |
| propylene | 50.1 | 52.6 | 51.8 | 49.6 | 44.3 | 44.3 |
| C3/C2 | 1.4 | 1.4 | 1.3 | 1.4 | 1.2 | 1.2 |
| C2 + C3 | 85.2 | 89.5 | 82.3 | 78.8 | 82.0 | 81.7 |

TABLE 2

|  | SAPO-18 | SAPO-34 |
|---|---|---|
|  | Morphology | |
|  | lamellas Ex 12 | laminated cubes comp ex IIIa |
| Methane in the MTO effluent | 2.0 | 2.5 |
| Purity C2's | 100 | 100 |
| Purity C3's | 100 | 98 |
| C3/C2 | 1.2 | 1.0 |
| C2 + C3 | 78.0 | 80.0 |
| ethylene in the MTO effluent | 36.0 | 41.0 |
| propylene in the MTO effluent | 42.0 | 39.0 |
| OCP feed | | |
| non cyclic olefins C4-C5 | | |
| from MTO effluent | | |
| C4 olefins | 15.0 | 12.5 |
| C5 olefins | 4.0 | 3.0 |
| Σ olefins sent to OCP | 19.0 | 15.5 |
| MTO + OCP | | |
| ethylene | 38.8 | 43.3 |
| propylene | 53.1 | 48.1 |
| C3/C2 | 1.4 | 1.1 |
| C2 + C3 | 91.9 | 91.4 |

The invention claimed is:

1. A process to make light olefins from a halogenide-containing or sulphur-containing organic feedstock comprising:
contacting said halogenide-containing or sulphur-containing organic feedstock in a primary reactor with a catalyst comprising a metalloaluminophosphate (MeAPO) molecular sieve at conditions effective to convert at least a portion of the feedstock to form a first reactor effluent comprising light olefins and a heavy hydrocarbon fraction;
separating said light olefins from said heavy hydrocarbon fraction; contacting said heavy hydrocarbon fraction in a second reactor at conditions effective to convert at least a portion of said heavy hydrocarbon fraction to light olefins;
wherein said MeAPO molecular sieve has an empirical chemical composition on an anhydrous basis, after synthesis and calcination, expressed by the formula $H_xMe_yAl_zP_kO_2$ in which,
y+z+k=1,
x is less than or equal to y,
y has a value ranging from 0.0008 to 0.4,
z has a value ranging from 0.25 to 0.67,
k has a value ranging from 0.2 to 0.67;
said MeAPO molecular sieve having predominantly a plate crystal morphology having a width (W) and a thickness (T) wherein W/T is greater than or equal to 10.

2. The process of claim 1, wherein y has a value from 0.005 to 0.18.

3. The process of claim 1, wherein z has a value from 0.38 to 0.55.

4. The process of claim 1, wherein k has a value from 0.36 to 0.54.

5. The process of claim 1, wherein y has a value ranging from 0.011 to 0.14, z has a value ranging from 0.40 to 0.55 and k has a value ranging from 0.38 to 0.54.

6. The process of claim 1, wherein Me is silicon.

7. The process of claim 1, wherein T is less than or equal to 0.15 μm.

8. The process of claim 1, wherein T is less than or equal to 0.10 μm.

9. The process of claim 1, wherein T is less than or equal to 0.08 μm.

10. The process of claim 1, wherein T ranges from 0.01 to 0.07 μm.

11. The process of claim 1, wherein T ranges from 0.01 to 0.04 μm.

12. The process of claim 1, wherein W/T ranges from 10 to 100.

13. The process of claim 1, wherein the structure is essentially CHA or AEI or a mixture thereof.

14. The process of claim 1, wherein the structure is essentially SAPO 18 or SAPO 34 or a mixture thereof.

15. A process to make light olefins from an oxygen-containing, halogenide-containing or sulphur-containing organic feedstock comprising:
contacting said oxygen-containing, halogenide-containing or sulphur-containing organic feedstock in a primary reactor with a catalyst made of a metalloaluminophosphate (MeAPO) molecular sieve at conditions effective to convert at least a portion of the feedstock to form a first reactor effluent comprising light olefins and a heavy hydrocarbon fraction;
separating said light olefins from said heavy hydrocarbon fraction;
contacting said heavy hydrocarbon fraction in a second reactor at conditions effective to convert at least a portion of said heavy hydrocarbon fraction to light olefins to form a second reactor effluent;
wherein said MeAPO has been prepared by a method comprising:
forming a reaction mixture containing a texture influencing agent (TIA), an organic templating agent (TEMP), at least one reactive inorganic source of $MeO_2$ essentially insoluble in the TIA, reactive sources of $Al_2O_3$ and $P_2O_5$
crystallizing the reaction mixture until crystals of the metalloaluminophosphate are formed,
recovering a solid reaction product,
washing the solid reaction product with water to remove the TIA, and
calcinating the washed solid reaction product to remove the organic template.

16. The process of claim 15, wherein said reaction mixture has a composition expressed in terms of molar oxide ratios of:
$TEMP/Al_2O_3$ ranges from 0.3 to 5.0,
$MeO_2/Al_2O_3$ ranges from 0.005 to 2.0,
$P_2O_5/Al_2O_3$ ranges from 0.5 to 2.0,
$TIA/Al_2O_3$ ranges from 3.0 to 30.

17. The process of claim 15, wherein the ratio $TEMP/Al_2O_3$ ranges from 0.5 to 2.0.

18. The process of claim 15, wherein the ratio $MeO_2/Al_2O_3$ ranges from 0.022 to 0.8.

19. The process of claim 15, wherein the ratio $P_2O_5/Al_2O_3$ ranges from 0.8 to 1.2.

20. The process of claim 15, wherein the ratio $TIA/Al_2O_3$ ranges from 6.0 to 20.

21. The process of claim 15, wherein Me is silicon.

22. The process of claim 15, wherein the texture influencing agent (TIA) is selected from the group consisting of 1,2-propanediol, 1,3-propanediol, methanol, ethanol, propanol, isopropanol, butanol, glycerol, ethylene glycol, or mixtures thereof.

23. The process of claim 15, wherein the structure is essentially CHA or AEI or a mixture thereof.

24. The process of claim 15, wherein the structure is essentially SAPO 18 or SAPO 34 or a mixture thereof.

25. The process of claim 15, wherein the oxygenate feedstock comprises methanol, dimethyl ether, or a mixture thereof.

26. The process of claim 15, wherein the catalyst of the second reactor comprises a crystalline silicate of the MFI family or the MEL family.

27. Process according to claim 26, wherein the catalyst is a ZSM-5 or a silicalite.

28. The process of claim 15, wherein ethylene, in whole or in part, coming from either or both of the first reactor effluent or the second reactor effluent is recycled back to the inlet of the first reactor.

29. The process of claim 15, wherein ethylene, in whole or in part, coming from either or both of the first reactor effluent or the second reactor effluent is recycled back to the inlet of the second reactor.

30. The process of claim 15, further comprising: the second reactor effluent is sent to a fractionator to separate light olefins from hydrocarbons having 4 carbon atoms or more; and said hydrocarbons having 4 carbon atoms or more are recycled at the inlet of the second reactor.

31. The process of claim 15, wherein the light olefins comprise ethylene that is further polymerized.

32. The process of claim 31, wherein the ethylene is further polymerized with one or more comonomers.

33. The process of claim 15, wherein the light olefins comprise propylene that is further polymerized.

34. The process of claim 15, wherein the propylene is further polymerized with one or more comonomers.

\* \* \* \* \*